United States Patent [19]
Basso, Jr. et al.

[11] Patent Number: 6,131,090
[45] Date of Patent: Oct. 10, 2000

[54] METHOD AND SYSTEM FOR PROVIDING CONTROLLED ACCESS TO INFORMATION STORED ON A PORTABLE RECORDING MEDIUM

[75] Inventors: Micheal R. Basso, Jr., Norwalk; Joonho Lee, Hamden; Chunhua Li, North Haven, all of Conn.

[73] Assignee: Pitney Bowes Inc., Stamford, Conn.

[21] Appl. No.: 08/810,746

[22] Filed: Mar. 4, 1997

[51] Int. Cl.[7] ................................................. G06F 17/60
[52] U.S. Cl. ........................ 706/23; 380/22; 600/300; 705/2; 705/3; 705/17; 705/18; 707/10; 235/380
[58] Field of Search ........................... 706/2, 3; 380/23, 380/22; 705/18, 17, 3

[56] References Cited

U.S. PATENT DOCUMENTS

| | | | |
|---|---|---|---|
| 4,236,332 | 12/1980 | Domo ................................... | 40/2.2 |
| 4,318,554 | 3/1982 | Anderson et al. ........................ | 283/7 |
| 4,438,824 | 3/1984 | Schloer ................................ | 178/22.08 |
| 4,567,600 | 1/1986 | Massey et al. .......................... | 375/2.1 |
| 4,632,428 | 12/1986 | Brown ................................... | 283/76 |
| 4,648,189 | 3/1987 | Michel .................................. | 40/546 |
| 4,692,394 | 9/1987 | Drexler ................................. | 430/140 |
| 4,707,592 | 11/1987 | Ware ................................... | 235/379 |
| 4,868,373 | 9/1989 | Opheij et al. .......................... | 235/380 |
| 4,868,376 | 9/1989 | Lessin et al. .......................... | 235/492 |
| 4,926,480 | 5/1990 | Chaum .................................. | 380/23 |
| 4,982,072 | 1/1991 | Takigami ............................... | 235/384 |
| 4,995,081 | 2/1991 | Leighton et al. ........................ | 380/23 |
| 5,124,920 | 6/1992 | Tamada et al. .......................... | 364/424.05 |
| 5,191,611 | 3/1993 | Lang ................................... | 380/25 |
| 5,197,763 | 3/1993 | Whalen ................................. | 283/76 |
| 5,215,334 | 6/1993 | Presson et al. ......................... | 283/76 |
| 5,224,163 | 6/1993 | Gasser et al. .......................... | 380/30 |
| 5,291,399 | 3/1994 | Chaco .................................. | 705/3 |
| 5,301,105 | 4/1994 | Cummings, Jr. ......................... | 364/401 |
| 5,325,294 | 6/1994 | Keene .................................. | 364/413.01 |
| 5,457,746 | 10/1995 | Dolphin ................................. | 706/51 |
| 5,495,533 | 2/1996 | Linehan et al. ......................... | 380/21 |
| 5,499,293 | 3/1996 | Behram et al. .......................... | 380/4 |
| 5,499,297 | 3/1996 | Boebert ................................ | 380/23 |
| 5,514,856 | 5/1996 | Kirahara et al. ........................ | 235/440 |
| 5,521,980 | 5/1996 | Brands et al. .......................... | 380/30 |
| 5,524,073 | 6/1996 | Stambler ............................... | 380/24 |
| 5,774,546 | 6/1998 | Handelman et al. ...................... | 380/4 |
| 5,832,488 | 11/1998 | Eberhardt ............................... | 707/10 |
| 5,867,821 | 2/1999 | Ballantyne et al. ...................... | 705/2 |

OTHER PUBLICATIONS

Dialog Bluesheets, pp. 151–1 to 151–4, 154–1 to 154–4, 156–1 to 156–6, 1998.
Bruce Schneier, Applied Cryptography, Second Edition: Protocols, Algorithms, and Source Code in C, Oct. 1995.
Lasercard Systems Corporation Document.

*Primary Examiner*—Tariq R. Hafiz
*Assistant Examiner*—Michael J. Pender, Jr.
*Attorney, Agent, or Firm*—Kimberly S. Chotkowski; Michael E. Melton

[57] ABSTRACT

A method and system for providing controlled access to information stored on a smartcard. The system includes a data processing center maintained by a trusted third party for storing a database of authorizations of various service providers to access information pertaining to individuals, and for responding to request by service providers for access from terminals which communicate with the data processing center and smartcards storing the individuals' information. The information is stored on the smartcard in encrypted form and the data processing center provides an access code, which includes a key for decrypting the information, only to service providers who are authorized to access the information. The service provider then sends the access code to the smartcard which verifies the access code and decrypts and outputs the requested information. The smartcard then computes a new key as a function of information unique to each access session and uses the new key to re-encrypt the information, and then erases the new key. The data processing center also computes the new key so that the data processing center can provide an access code including the new key for the next request for access.

22 Claims, 8 Drawing Sheets

METHOD AND SYSTEM FOR PROVIDING CONTROLLED ACCESS TO INFORMATION STORED ON A PORTABLE RECORDING MEDIUM

BACKGROUND OF THE INVENTION

The subject invention relates to a method and apparatus for storing information and controlling access to that information. More particularly, it relates to a method and apparatus for securely storing information of a sensitive character, such as medical histories, and controlling access to that information so as to limit access to persons or organizations which are authorized access.

The subject invention relates to the field of, and may contain elements of disclosure similar to elements disclosed in commonly assigned U.S. patent application Ser. No. 08/810,057 by: Melvin J. Scolnick, for: KEY MANAGEMENT SYSTEM FOR USE WITH SMART CARD (attorney doc. E-595) filed on even date herewith.

Social, economic, and technical changes have combined to substantially reduce the role played by the family doctor; the general practitioner who provided most of a patient's care over a substantial period of time, and who was an effective custodian of the patient's medical records. As medical practice shifts from the traditional fee-for-service basis to HMO's and "networks" of physicians and competition between these organizations grows ever more intense, employee/patients change or lose their jobs and thus change or loose their access to particular health care organizations, and both business and recreational travel continue to increase, it becomes increasingly less effective to rely upon a family doctor as the custodian of a patient's medical records. For these and other reasons there has been a long felt need for a mechanism whereby appropriate medical personal can quickly access a patient's medical records.

One approach to this problem has been to propose systems where a third party would maintain a database of medical records which could be accessed from remote terminals located in physician's offices, hospitals and the like. Such systems are proposed, for example in U.S. Pat. No. 5,325,294 to: Keene, for: Medical Privacy System, issued: Jun. 28, 1994 and U.S. Pat. No. 5,301,105 to: Cummings, Jr., for: All Care Health Management System, issued: Apr. 5, 1994.

While such systems may prove adequate to disseminate medical records it is apparent that they suffer from the problems common to all large database systems. The party charged with maintaining such a database must have the capability to assure the accuracy of the information in the database and that the information is updated in a timely manner, provide security for the system, assure that authorized users can access the system in a timely manner, and, most importantly, assure that access is limited to authorized users. As a result there is a reluctance to entrust sensitive data to a single, or a small number of, databases; particularly where information is as sensitive as that contained in medical records.

The converse to the central database approach is for each patient to carry his or her own medical records. In its simplest form this approach involves dog tags or bracelets worn by the patient, which identify the patient's blood type, allergies, or the like. While this approach is effective for limited information, such as blood type, clearly the vast majority of patients would not willingly wear or carry something which identified them as HIV positive or having Hansen's disease.

One approach to overcoming this problem is proposed in U.S. Pat. No. 5,499,293 to: Behram et al., for: Privacy Protected Information Medium Using a Data Compression Method, issued Mar. 12, 1996. Behram et al. discloses a system where medical information is recorded in compressed form on a card carried by a patient. The compression algorithm used both reduces the amount of storage needed on the card and makes access to the information difficult for a person who does not have access to a special dictionary to decompress the information. While this may alleviate storage requirements, the problem of maintaining confidentiality of the medical records stored on the card remains, since, if the needed dictionary is widely distributed, a lost or stolen card can easily be accessed, while if the distribution of the dictionary is tightly controlled the card may fail of its purpose. Further, even if the patient is somehow provided with a password or key necessary to access the card, the card may still fail of its purpose if the patient is unconscious or otherwise unable to provide the password or key.

Thus, it is an object of the subject invention to provide a method and apparatus for storing information such as medical records in a manner which is secure against unauthorized access yet widely and readily accessible by authorized persons or organizations.

BRIEF SUMMARY OF THE INVENTION

The above object is achieved and the disadvantages of the prior art are overcome in accordance with the subject invention by means of a system and method for recording information and controlling access to that information. The system includes a portable recording medium, which includes memory for storing information and a microprocessor responsive to input of an access code to enable access to the memory or a predetermined portion of the memory; a data processing center which includes a database of authorizations of a plurality of service providers with respect to the information; and a terminal which communicates with the data processing center. The data processing center is responsive to a message from the terminal which identifies a service provider seeking access to the information by accessing the database to determine if the service provider is authorized to access the information, and by outputting the access code to the service provider only if the service provider is authorized to access the information.

The system is used to control access to information recorded on the portable recording medium by establishing the data processing center as secure, and by then receiving data identifying various service providers who can request access to the information, and verifying this data. A database is then established in the data processing center identifying the authorizations of each service provider with respect to the information. When a message is received from one of the service providers requesting access to the information the data processing center accesses the database to determine if that service provider is authorized to access the information, and, if so, provides the service provider with the necessary access code.

In accordance with one aspect of the subject invention a different key is required to decrypt the information each time the information is accessed.

In accordance with another aspect of the subject invention a certifying authority certifies each service provider authorized to access the information, and messages requesting access to the information from a service provider are digitally signed by the service provider with a private key certified to the service provider by the certifying authority.

In accordance with another aspect of the subject invention, the digitally signed messages are encrypted, preferably with the certified private key.

(As used in here "digitally signed" is intended to include any use of encryption techniques to provide assurance that a message actually originated with its putative originator. "Certificate", as the term is used herein and understood by those skilled in the art, means an encrypted message which is evidence of the assurance of a "Certifying Authority" that another encrypted message to which the certificate relates actually originated with a third party identified by the Certificate.)

In accordance with another aspect of the subject invention the portable recording medium is a smartcard.

In accordance with still another aspect of the subject invention the portable recording medium includes a writable optical memory.

In accordance with still another aspect of the subject invention the information is medical information.

In accordance with still another aspect of the subject invention the data processing center will respond to a message from a service provider seeking emergency access to the information to provide the access code without regard to authorization of the service provider, and will then record, at least, a time for the request and the identity of the service provider making the emergency request.

In accordance with yet another aspect of the subject invention information stored on the portable recording medium is encrypted with a current session key and the access code includes the current session key, and the microprocessor is responsive to input of the access code to determine the current session key, decrypt the information and output the decrypted information.

In accordance with still yet another aspect of the subject invention the information is then re-encrypted with a next session key and rewritten to the memory. The next session key is determined as a predetermined function of access session information which is unique to each session of access to the information.

In accordance with still yet another aspect of the subject invention after re-encrypting the information the microprocessor deletes the next session key so that the information cannot be again accessed until a new access code is received.

Thus it is apparent to those skilled in the art that the subject invention advantageously achieves the above object and overcomes the disadvantages of the prior art. Other objects and advantages of the subject invention will be apparent to those skilled in the art from consideration of the attached drawings and the detailed description set forth below.

DETAILED DESCRIPTION OF PREFERRED EMBODIMENTS OF THE SUBJECT INVENTION

The following terms used herein are defined as follows:

| | |
|---|---|
| ACODE | Access Code issued by a Trusted Authority to allow access to information stored in accordance with the subject invention. ACODE includes the Current Session Key as well as other information relating to the current access session. |
| CA | A Certifying Authority which issues Certificates to authenticate identity. |
| CERT(x) | Certificate of x; CERT(x) = Pr(CA)[Pb(x), ID(x)] |
| CSK | Current Session Key - Secret key used to decrypt information read from storage during current session. CSK[CSK[M]] = M  CSK = NSK of previous session |
| H | A service provider such as a hospital or, more generally, any party seeking access to information secured in accordance with the subject invention. |
| K | Function used to derive NSK from access session information in ACODE (as well as possibly other information). NSK = K(ACODE) |
| key(x)[M] | M encrypted or decrypted, as indicated by context, with key(x). |
| NSK | Next Session Key - Secret key used to encrypt information written to storage during current session. NSK[NSK[M]] = M |
| P | A party such as an individual Patient or, more generally, any party seeking to store information in a secure manner while permitting access to such information only to authorized parties. |

-continued

| | |
|---|---|
| Pb(x) | The public key of x - published or otherwise available. |
| Pr(x) | The private key of x - held in secret by x. |
| Pb(x)[M](Pr(x)[M]) | M encrypted with the public(private) key of x. |
| Pr(x)[Pb(x)[M]](Pb(x)[Pr(x)[M]]) | M encrypted with the public(private) key of x and decrypted with the private(public) key of x = M. M cannot be found from Pb(x), Pb(x)[M] or Pr(x), Pr(x)[M]; Pr(x)(Pb(x)) cannot be found from Pb(x)[M], M, Pb(x)[M'], M' . . . (Pr(x)[M], M, Pr(x)[M'], M' . . . ) |
| TA | Trusted Authority which maintains database of authorizations granted by P and grants or denies requests for access. |

Figure 1:
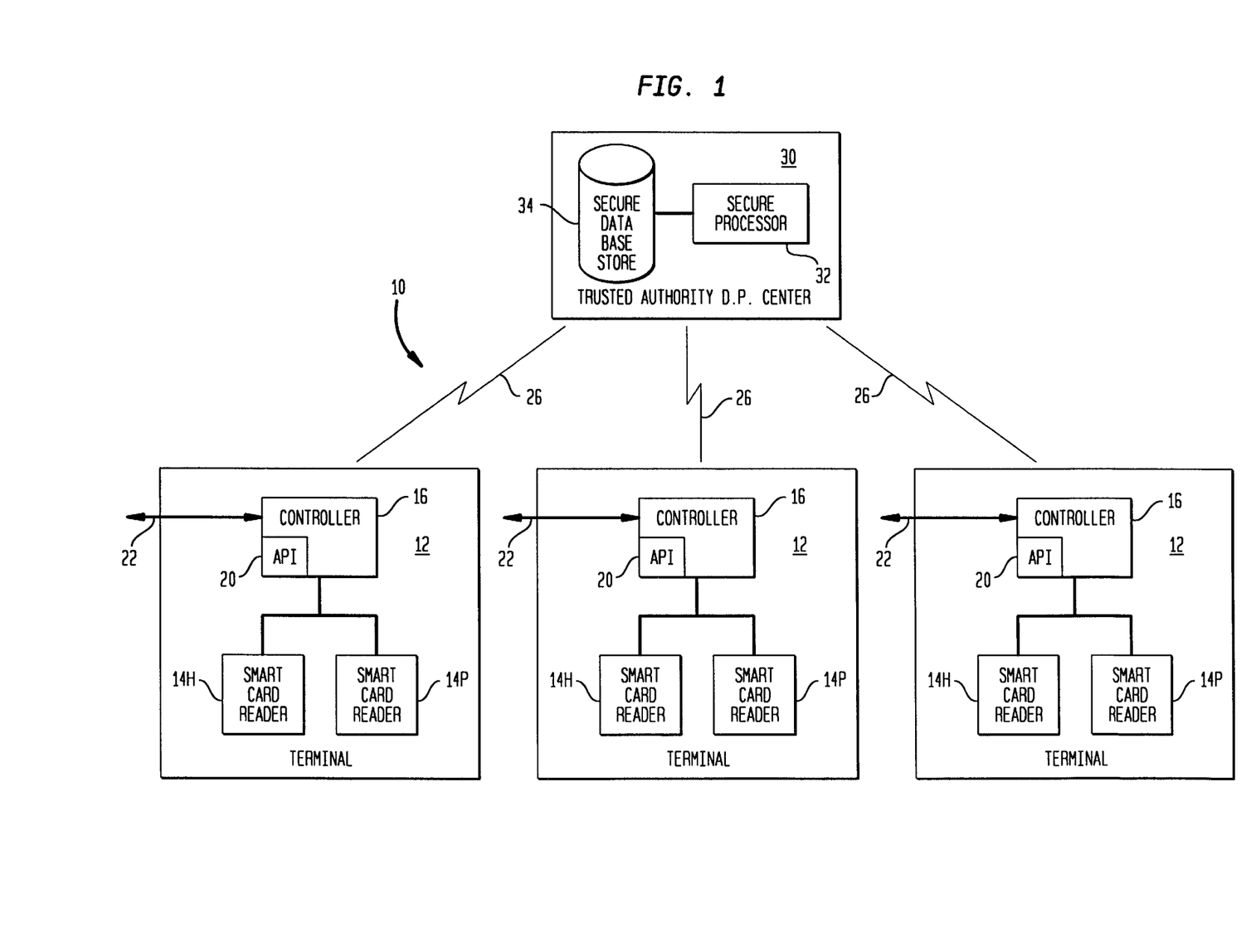
FIG. 1 is a schematic block diagram of a system in accordance with the subject invention.

FIG. 1 shows network 10 for controlling access to information stored on a smartcard. In the embodiment shown, the information includes medical information. Network 10 includes a plurality of terminals 12 which are located at the facilities of various health service providers, such as doctors office's, hospital emergency rooms, other hospital services, ambulances, and nursing homes; as well as at other organizations involved in healthcare such as insurance companies.

Terminals 12 each comprise a pair of smartcard readers 14h and 14p for reading information from, and writing information to, the smartcards of service provider H or an individual P seeking medical services. The smartcard of individual P includes medical information or other information such as insurance information together with encryption keys, certificates and other data needed to control access to the medical information, while the smartcard of provider H includes encryption keys, certificates and other information needed to obtain access to the medical information, as will be described further below.

(While terminals 12 have been shown with 2 smartcard readers primarily for ease of description, it will be apparent to those skilled in the art that a single reader could be used to read both smartcards sequentially, or that information for provider H could be stored permanently in terminal 12. However, it is preferred that at least part of the information needed by provider H to access information on the smartcard of individual P be stored on one or more smartcards to increase security and to allow individual users of terminal 12 to be identified.)

Terminals 12 also each include controllers 16 for controlling operation of terminal 12 in accordance with an Access Protection Interface (API) program 20, as will be described further below.

Terminals 12 also includes conventional I/O 22 for output of data from, or input of data to, the smartcard of individual P, in any convenient manner.

Terminals 12 communicate through links 26 (which can comprise any convenient form of communications) with data processing center 30 of a Trusted Authority. Data processing center 30 includes secure processor 32 and secure database store 34 which are maintained and operated in a manner which assures the integrity of operation of data processing center 30. Database store 34 stores a database of authorizations for particular providers H to access information of particular individuals P and data processing center 30 will respond to requests from particular providers H for access to the information of particular individuals P only if proper authorization is found in database store 34.

(While the embodiment described herein assumes for ease of description that only a single type of information is stored on the smartcard of each individual P, those skilled in the art will readily recognize that information stored for an individual P maybe partitioned in any convenient manner and authorizations for access to various groups and subgroups of information can readily be processed separately and independently by data processing center 30. Thus, other types of information, such as financial information, or licensees or authorizations can be stored on a single smartcard with access separately controlled in accordance with the subject invention.)

(By Trusted Authority herein is meant a party who is trusted by both providers H and individuals P to maintain the integrity of a system in accordance with the subject invention and to operate that system in accordance with the understandings of the parties so that authorized providers H, and only authorized providers H, are provided with prompt, accurate access to information. Ultimately, of course, such trust can be established only through a wide spread reputation for integrity. However, individuals or organizations which do not have a well established reputation can operate data processing center 30 if they are "certified" by well established individuals or organizations (hereinafter Certifying Authority), as will be described further below.)

Figure 2:
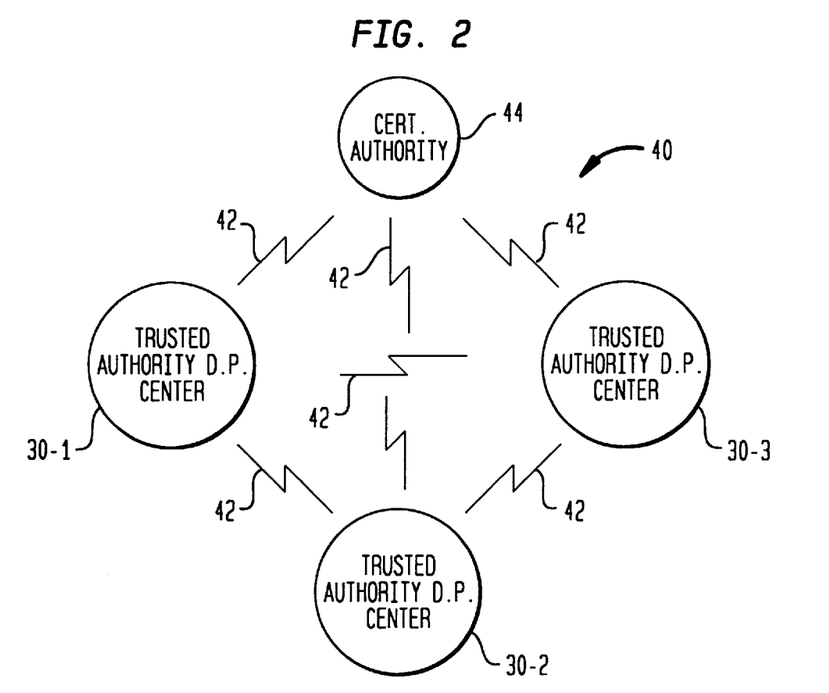
FIG. 2 is a schematic diagram of a network of data processing centers operated by Trusted Authorities to provide access codes to authorized service providers seeking access to information, and a Certifying Authority.

Those skilled in the art will recognize that it is impractical for a single data processing center 30 to maintain a database of authorizations for all individuals P who might wish to make use of the benefits of the subject invention. Thus FIG. 2 shows a plurality of Trusted Authority data processing centers 30-1, 30-2 and 30-3 which would each maintain a database of authorizations for individuals P residing in a given region. Since it would also be financially and operationally difficult to operate such a network on a national or world-wide basis, which would of course include many more than three data processing centers, and since a particular Trusted Authority in a particular region maybe new to the industry, or may not be widely known, network 40 includes Certifying Authority 44 operatively connected via network communication 22, which is assumed to have a well known reputation for integrity and efficiency, which certifies data processing centers 30-1, 30-2 and 30-3 in a manner more fully described below, after assuring itself that the centers will be operated properly.

In other preferred embodiments of the subject invention there can be a plurality of Certifying Authorities, which may be ordered in a hierarchy, with higher ranking Authorities certifying lower ranking Authorities. In still other embodiments Certifying Authorities can be associated (e.g. operated by the same entity) with Trusted Authorities. Typically such associated Certifying Authorities would provide key pairs and Certificates to service providers and individuals whose records were in the custody of the associated Trusted Authority.

Figure 3:
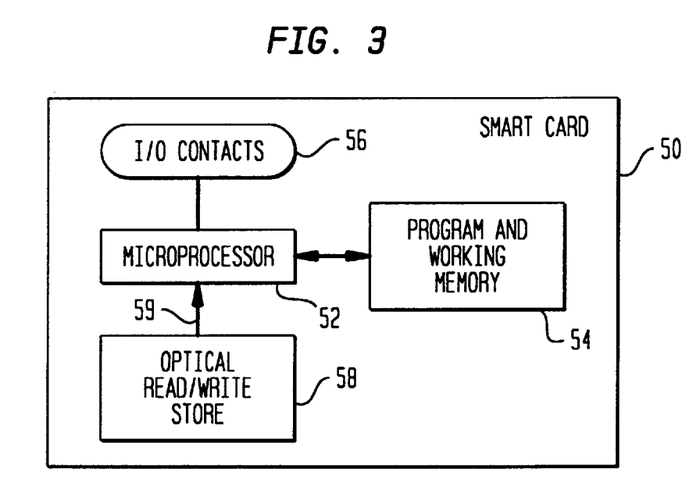
FIG. 3 is a schematic block diagram of a smartcard suitable for use in the system of the subject invention.

FIG. 3 shows a schematic block diagram of a high capacity smartcard suitable for use with one embodiment of the subject invention. In FIG. 3 smartcard 50 includes a conventional microprocessor 52 which communicates with conventional program and working memory 54, and includes I/O contacts 56 for communication between microprocessor 52 and card reader 14p. Smartcard 50 also includes an optical read/write store 58. Since there is no direct communication between store 58 and microprocessor 52 data is transferred between store 58 and microprocessor 52 through card reader 14p. Accordingly, security of data in store 52 relies upon encryption of the data by microprocessor 52, as will be described further below. Smartcards substantially similar to smartcard 50, as well as compatible readers, are commercially available from Lasercard Systems Corporation, Mountain View Calif. (a subsidiary of Drexler Technology Corporation), and are described in an electrically published document LASERCARD SYSTEMS Technical Information http://www.lasercard.com/lsctec0.html, and need not be discussed further here for an understanding of the subject invention.

(While there is no direct communication between microprocessor 58 and read/write store 58, in a preferred embodiment microprocessor 58 monitors electrical parameters of store 58, in a known manner, through connection 59 to detect signs of physical tampering. In the event tampering is detected microprocessor 52 can disable data output or initiate other appropriate responses to alert users to the possibility that data has been compromised.)

It should be noted that cards used by providers H will not generally store large quantities of information and simpler smartcards or memory cards and corresponding readers 14h maybe used by providers H.

Figure 4:
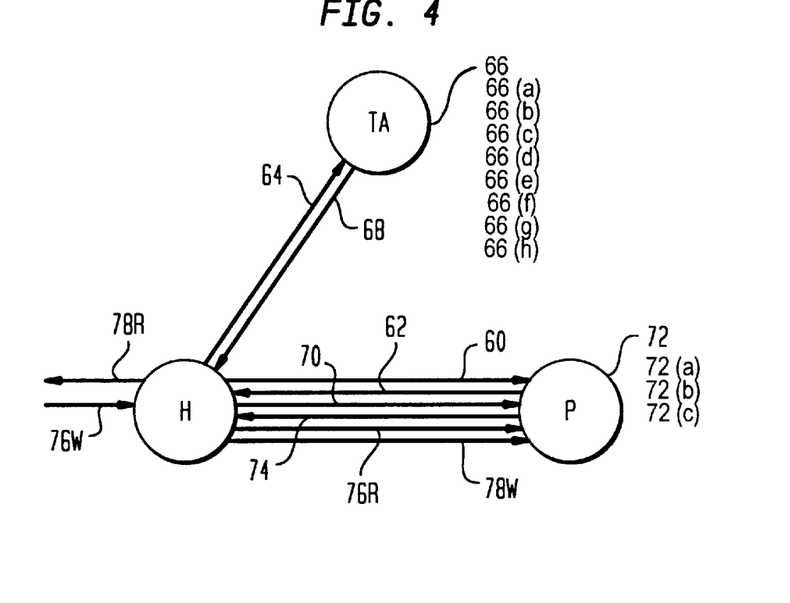
FIG. 4 is a schematic diagram of data flows among a service provider seeking access to information pertaining to an individual, a smartcard belonging to that individual, and the Trusted Authority which communicates with the service provider and maintains a database of authorizations issued by the individual.

Turning to FIG. 4, a data flow chart for access by a provider H to medical or other data of an individual P, where authorizations granted by individual P are stored at the Trusted Authority data processing center which communicates with provider H.

Table 1 shows data which is initially provided to the Trusted Authority, provider H and individual P; more particularly the data which is stored in Data processing center 30, terminal 12 (or which is uploaded from the smartcard of provider H to terminal 12), and the smartcard of individual P.

Assuming that the smartcard of individual P has been inserted into reader 14p, and that necessary information has been uploaded from the smartcard of provider H to terminal 12, then at 60 provider H sends a start signal to individual P.

TABLE 1

Initialization

TA:

| | |
|---|---|
| Pr(TA), Pb(TA) | Public private key pair from CA |
| CERT(TA) | Pr(CA) [Pb(TA), ID(TA)] |
| Pb(CA) | CA public key |
| K | Session key update function |
| Data Base | Authorization (H, P), initial CSK (P) |

H:

API

| | |
|---|---|
| Pr(H), Pb (H)[(1)] | Public key pair from CA |
| CERT(H)[(1)] | Pr (CA) [Pb(H), ID(H)] |
| Pb(CA) | CA public key |
| ID(U) | Optional user ID |

P:

| | |
|---|---|
| Pr(P), Pb(P)[(1)] | Public key pair from CA |
| CERT (P)[(1)] | Pr(CA) [Pb(P), ID(P)] |
| Pb(CA) | CA public key |
| K | Session key update function |

TABLE 1-continued

Initialization

| | |
|---|---|
| ID(TAp)[(2)] | ID of TA with custody of authorizations granted by P |

[(1)]A single CA which provides all certificates and key pairs has been assumed for ease of description. More typically, as described above, the subject invention contemplates multiple CA's, some or all of which may be associated with or function as TA's, where each user (H or P) will be initialized by the TA with which it is associated. CA's, in turn, can be certified by higher authorities such as governments.
[(2)]Not necessary in single TA systems.
At 62, individual P returns: (62) CERT(P)

Thus, at 62 individual P returns a certificate which has been issued by a Certifying Authority, which in a small network having only a single Trusted Authority can be that Trusted Authority. Then at 64:

| | |
|---|---|
| (64) | Pr(H) [CERT(P), DATA REQUEST], CERT(H) |

Terminal 12 receives the certificate of individual P and forms a message by appending a data request for access and encrypting the combination with the private key of provider H, and appending the certificate of provider H. The request for data access will indicate whether the access is to read data or to write data. Also, as noted above, data stored on the smartcard of individual P may be partitioned in any convenient manner and the data access request will then indicate what group or subgroup of data is to be accessed.

At 66 the Trusted Authority receives and processes the message from provider H as follows:

| | |
|---|---|
| At (66) (a) | Pb(CA) [CERT(H)] = Pb(H), ID(H) |

Processor 32 decrypts the certificate of provider H with the public key of the Certifying Authority to obtain the public key and the identification of provider H. It should be noted that the public key is unique to provider H and other information needed could be obtained from a database table, however, it is preferable for efficiency of operation to include identification in the certificate, also preferably, this identification should characterize provider H since frequently individuals P will wish to authorize access for a certain class of provider; e.g. all emergency rooms.

| | |
|---|---|
| At (66) (b) | Pb(H) [Pr(H) [CERT(P), DATA REQUEST] = CERT(P), DATA REQUEST |

Processor 32 then uses the public key of provider H to obtain the certificate of individual P and the request for data access.

| | |
|---|---|
| At (66) (c) | Pb(CA) [CERT(P)] = Pb(P), ID(P) |

Processor 32 then uses the public key of the Certifying Authority to obtain the public key of individual P and the identification of individual P from the certificate for individual P.

| At (66) (d) | Query (ID(P), ID(H), DATA REQUEST) |
|---|---|

Processor 32 then queries database 34 to determine if individual P has authorized provider H (or that class of service provider) for the type of data access requested.

| At (66) (e) | Response (CSK) |
|---|---|

Assuming that the data access requested is authorized the Current Session Key is returned from database 34. (CSK=NSK of previous session). If the data access requested is not authorized the system will enter an error routine to indicate access denied.

| At (66) (f) | ACODE = (Data Block Addr, Size, Date-Time, R/W, CSK) |
|---|---|

Processor 32 then forms message ACODE which, in a preferred embodiment, includes session information such as a data block address and size, the date and time, whether a read or write access is authorized; and the Current Session Key.

| At (66) (h) | K (ACODE) = NSK → Data Base |
|---|---|

Processor 32 then applies function K to current access session information to generate the next session key and the next session key is used to update the current session key in database 34. Access session information is unique to a particular access session and preferably includes at least a part of the information in ACODE. In other embodiments access session information can include information such as ID(H), ID(P), or an access sequence number which uniquely identifies each access session.

In other preferred embodiments of the subject invention processor 32 stores ACODE, or necessary parts of ACODE (i.e. session information and CSK for the session during which the "seed" is stored), or a derivative of such information such as "hash function" of such information at 66h as a "seed" from which CSK can be computed for the next session. Processor 32 can compute CSK for the next session or, in other embodiments, incorporate the "seed" into ACODE for the next session so that CSK for the next session can be computed by processor 52 of card 50. In such embodiments ACODE includes current session information and the "seed", which is used to compute CSK for the current session. CSK and the current session information from ACODE (which correspond to the updated "seed" stored by TA during the current session) are then used to compute NSK for the current session.

Such embodiments may offer increased security since neither NSK or CSK is explicitly stored either on card 50 or in database 34.

| At (68) | Pb(P)[Pr(TA)[ACODE],CERT (TA)] |
|---|---|

At 68 processor 32 encrypts ACODE with the Trusted Authority's private key and appends the Trusted Authority's certificate, and then encrypts the entire message with the public key of individual P, and sends the encrypted message to terminal 12 of provider H.

| At (70) | Pb (P) [Pr(TA) [ACODE], CERT(TA)] |
|---|---|

Terminal 12 forwards the encrypted message to the smartcard of individual P.

At 72 the smartcard of individual P processes the message as follows:

| At (72) (a) | Pr(P) [Pb(P)[Pr(TA) [ACODE], CERT(TA)]] = Pr(TA) [ACODE], CERT(TA) |
|---|---|

The smartcard uses the private key of individual P to decrypt the message and recover the encryption of ACODE and the certificate of the Trusted Authority.

| At (72) (b) | PB(CA)[CERT(TA)] = Pb(TA), ID(TA) |
|---|---|

The smartcard then uses the public key of the Certifying Authority to decrypt the certificate of the Trusted Authority to obtain the public key of the Trusted Authority and the Identification of the Trusted Authority.

| At (72) (c) | Pb(TA)[Pr(TA)[ACODE]] = ACODE = (Data Block Addr, Size, Date - Time R/W, CSK) |
|---|---|

The smartcard then uses the public key of Trusted Authority to decrypt ACODE which, in a preferred embodiment, will include a data block address and size, the date and time, whether the access is a read or write access, and the Current Session Key. Successful decryption of ACODE provides assurance that ACODE was obtain from the Trusted Authority and encrypted by the Trusted authority using a private key provided by the Certifying Authority.

| (74) | Data Block Addr, Size |
|---|---|

The smartcard of individual P then returns the Data Block Address and Size to terminal 12. As noted above, read/write operations to Optical Data Store 58 are carried out by terminal 12.

Then, assuming a read operation is to be carried out the data block is processed in segments as follows:

| | |
|---|---|
| At (76R) | Read, Decrypt and Re-encrypt, Rewrite and Assemble Data Segments from Optical Store 58 |
| At (78R) | Output Decrypted Data |

Typically data is encrypted and decrypted in segments of a given size. Since generally a data block will contain more then one segment the data is read as segments by terminal 12 sent to the smartcard where it is decrypted and re-encrypted with a New Session Key and both the decrypted segment and the re-encryption of the segment are returned to terminal 12, which rewrites the re-encrypted segment to optical store 58 and assembles the decrypted segments to form a decrypted data block. The decrypted Data Block is then output at 78r. the output data may then be displayed, processed or retransmitted in any convenient manner.

To input or update data segments are processed as follows:

| | |
|---|---|
| At (76W) | InputNewData |
| At (78W) | Encrypt New Data Segments and Write Encrypted Segments to Optical Store 58 |

When data is to be written or updated the new data is first input to terminal 12 which sends data segments to the smartcard where they are encrypted with the New Session Key and returned to terminal 12 which writes them to optical store 58. A more detailed description of the operation of the smartcard and terminal 12 in processing the data is set forth below.

The above description is based on the assumption that provider H is in communication with the Trusted Authority which maintains the database of authorizations granted by individual P. In general, in modern society where individuals relocate often and travel frequently, this will not be the case. In one embodiment of the subject invention, when a provider such as a hospital deals with an individual such as a new patient whose records of authorizations are maintained by a remote Trusted Authority the provider could access the remote Trusted Authority over the telephone network, in the manner described above. However, in a preferred embodiment, providers such as hospitals are connected to local Trusted Authorities by a dedicated links between terminal 12 and data processing center 30. This will provide high speed access for the normal situation where an individual known to the provider requests service and the data base of authorizations for that individual is maintained locally. In other situations, such as a strange patient who requires emergency medical services, requests for access to data are transmitted between the Trusted Authority in communication with the hospital and the remote Trusted Authority who maintains the database of authorizations granted by the individual, as is described more fully below with respect to FIG. 5.

Figure 5:
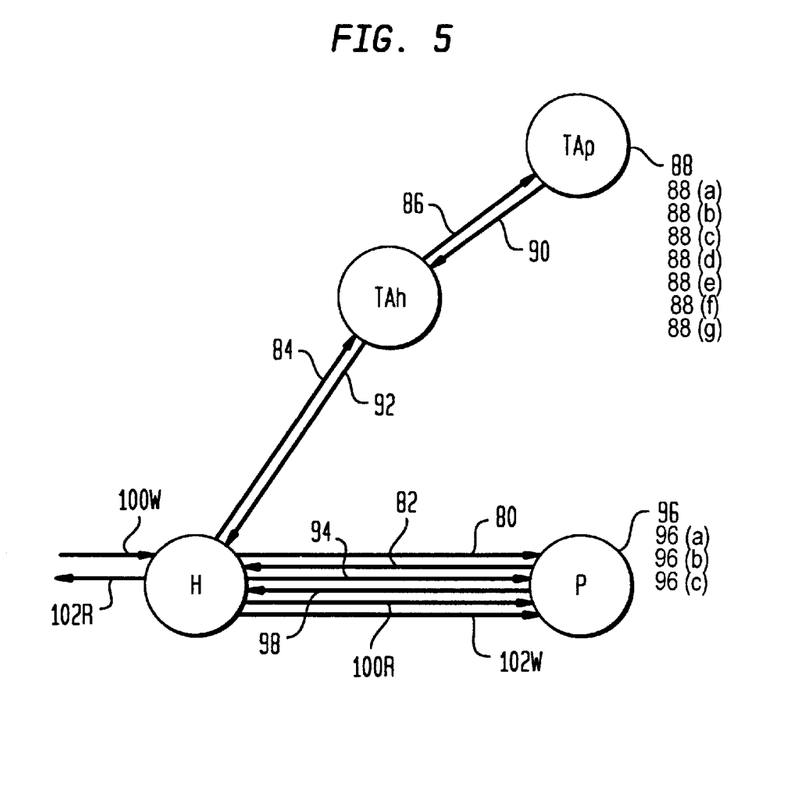
FIG. 5 is a similar representation of data flows where the Trusted Authority which maintains the database of authorizations is distinct from the Trusted Authority communicating with the service provider.

Turning to FIG. 5 with a initialization as shown in Table 1, at 80 terminal 12 of provider H sends a Start signal to the smartcard of the individual P, which has been connected to terminal 12. Then at:

| | |
|---|---|
| (82) | CERT(P), ID(TAp) |

At 82 the smartcard returns the certificate of individual P and the identification of the Trusted Authority which maintains the records of authorizations granted by individual P. Then at:

| | |
|---|---|
| (84) | Pr(H) [CERT(P), DATA REQUEST], ID(TAp), CERT(H), |

At 84 terminal 12 encrypts the certificate of individual P and the request for data access with the private key of provider H, appends the identification of the Trusted Authority of individual P and the certificate of provider H and sends this to the data processing center 30 of the Trusted Authority associated with provider H. Then at:

| | |
|---|---|
| (86) | Pr(H) [CERT(P], DATA REQUEST], ID (TAp), CERT(H), ID(TAh) |

Assuming that Trusted Authority associated with provider H is distinct from the Trusted Authority which maintains the database including the records of authorizations granted by individual P, at 86 the Trusted Authority associated with provider H appends its identification to the message received from provider H and sends this message to the Trusted Authority of individual P. Communication between Trusted Authorities can be in any convenient manner, such as over the switched telephone network, dedicated lines, or over a computer communications networks such as the Internet. Then at:

| | | |
|---|---|---|
| (88) | (a) | Pb(CA) [CERT(H)]= Pb(H), ID(H) |
| | (b) | PB(H) [Pr(H)[CERT(P), DATA REQUEST] = CERT(P), DATA REQUEST |
| | (c) | PB(CA) [CERT(P)] = Pb(P), ID(P) |
| | (d) | Query (ID(P), ID(H), DATA REQUEST) |
| | (e) | Response (CSK) |
| | (f) | ACODE = (DATA BLOCK ADDR, SIZE DATE-TIME; R/W, CSK) |
| | (g) | K (ACODE) = NSK → DATA BASE |

At 88, the Trusted Authority of individual P determines if the requested data access is authorized, and, if so, generates an access code and updates the current session key in a manner substantially identical to that described at (66) in FIG. 4. Then at:

| | |
|---|---|
| (90) | Pb(P) [Pr(TAp) [ACODE], CERT (TAp)], ID(H), ID(P) |

At 90, the Trusted Authority of P encrypts ACODE with its private key and appends its certificate, encrypts the combination with the public key of individual P, and appends the identifications of individual P and provider H, and returns this message to Trusted Authority associated with provider H. Then at:

| | |
|---|---|
| (92) | Pb(P) [Pr(TAp) [ACODE], CERT(TAp)], ID(p) |
| (94) | Pb(P) [Pr(TAp) [ACODE], CERT(TAp)] |

At 92, the Trusted Authority associated with provider H drops the identification of provider H and, at 94, forwards the message to the smartcard of individual P. Then, at:

| | |
|---|---|
| (96) | (a) Pr(P) [Pb(P) [Pr(TAp) [ACODE], CERT(TAp)] = Pr(TAp) [ACODE], CERT(TAp)<br>(b) Pb(CA) [CERT (TAp)] = Pb(TAp), ID(TAp)<br>(c) Pb(TAp) [Pr(TAp) [ACODE] = ACODE =<br>(Data Block Addr, Size; Date-Time; R/W (CSK) |
| (98) | Data Block, Addr, Size |
| (100r) | Read, Decrypt and Re-encrypt, Rewrite and Assemble Data Segments From Optical Store 58 |
| (102r) | Output Decrypted Data |
| (100w) | Input New Data |
| (102w) | Encrypt New Data SegmentsFrom Optical Store 58 and Write Encrypted Segments to Optical Store 58 |

At 96 through 102 terminal 12 and the smartcard of individual P interact to process data access in a manner substantially identical to that described with respect to 72–78 of FIG. 4.

In other embodiments of the subject invention the smartcard of individual P need not be connected to the terminal of the service provider who is requesting data access. It will be readily apparent to those skilled in the art that a service provider may request data access to a smartcard connected to a remote terminal, which in turn can be connected to the data processing center of either the Trusted Authority associated with that service provider or to another data processing center, with only minor modifications, readily apparent to those skilled in the art, to the communications protocols described above.

In another embodiment of the subject invention this capability is used to provide a novel means of secure communication. In accordance with this embodiment a first provider could request access to the smartcard of an individual to write data to a particular location. A second provider could then request access to that location to read the data, either during a single transaction or in a separate transaction. The second party would have assurance that the data had originated with a particular service provider, and with the authorization of a particular individual.

For example, if provider H were a hospital desiring to know the insurance status of individual P who was requesting medical services, provider H could write a query to the smartcard of individual P and the insurance company could then read that query from the smartcard of individual P. The insurance company would then be assured that the query had originated with provider H and was transmitted with the authorization of individual P.

Those skilled in the art will recognize that additional communications needed to initiate and coordinate various communications transaction in the embodiment just described can be carried out in any convenient manner and need not be described further here for an understanding of the subject invention.

FIGS. 6a and 6b, and 7a and 7b show the interaction of terminal 12 and the smartcard of individual P in reading data where the smartcard is smartcard 50 as shown in FIG. 3.

Figure 6A:
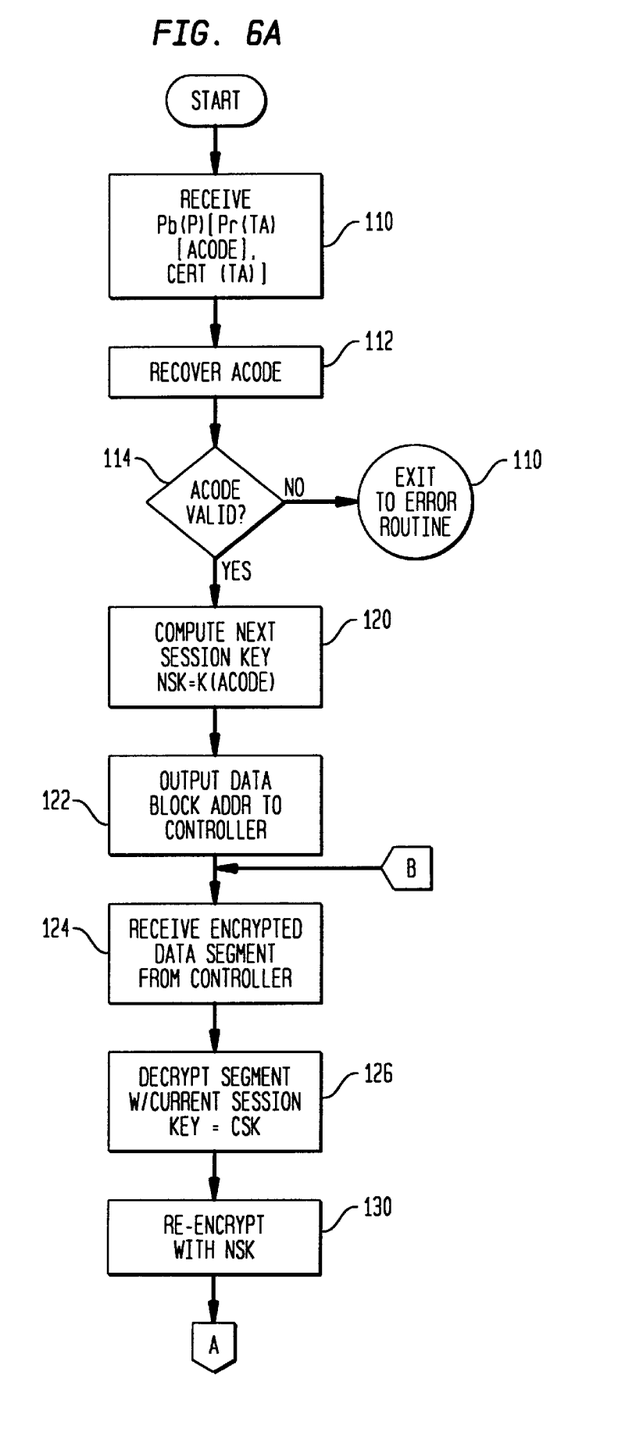
FIGS. 6a and 6b show a flow diagram of the operation of the smartcard of FIG. 3 when information is read from the smartcard.
Figure 6B:
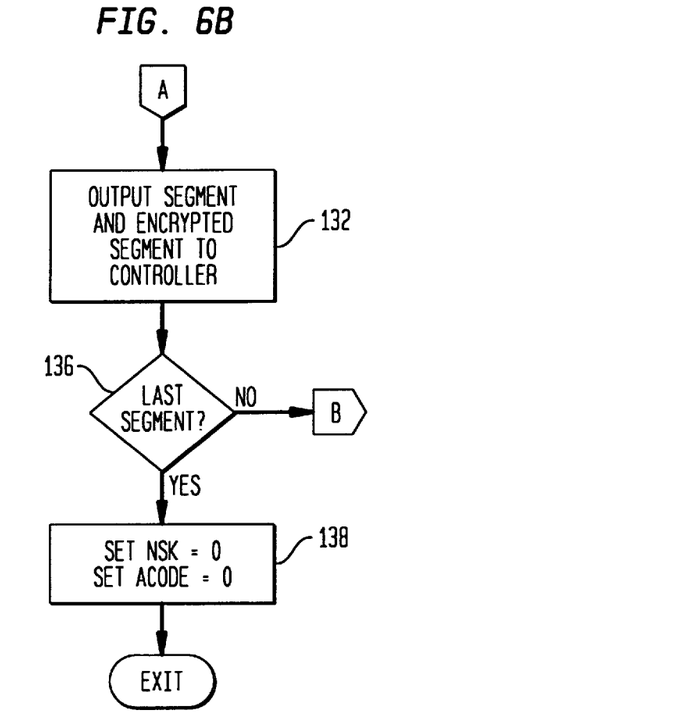

Turning to FIGS. 6a and 6b, at 110 smartcard 50 receives the encryption of ACODE and the certificate of the Trusted Authority which maintains records of authorizations granted by individual P as described above with respect to step 70 in FIG. 4 and step 94 in FIG. 5. At 112 smartcard 50 recovers ACODE as also described above. Then at 114 smartcard 50 determines if ACODE is valid. Preferably this is done by simply determining if ACODE is meaningful since the probability of an improperly decrypted message being intelligible is vanishingly small. If ACODE is not valid smartcard 50 exits to an error routine at 116.

Then, at 120, smartcard 50 computes the Next Session Key (NSK) in accordance with a predetermined function K, which is applied to information in ACODE. In a preferred embodiment function K comprises encryption with the private key Pr(P) of individual P.

Then, at 122, smartcard 50 outputs the data block address and size to terminal 12.

Then, at 124, smartcard 50 receives an encrypted data segment from terminal 12. At 128 it decrypts the segment with the Current Session Key (CSK), and at 130 re-encrypts the decrypted data with NSK. At 132 smartcard 50 outputs the decrypted segment and the re-encrypted segment to controller 16. At 136 smartcard 50 tests to determine if this is the last segment and, if not, returns to 124 to receive the next data segment.

After the last data segment is received, at 138 smartcard 50 sets NSK and ACODE to 0.

It should be noted that by deleting NSK and ACODE from the smartcard a high degree of security is achieved even for smartcards such as smartcard 50 where Optical Data Store 58 is necessarily accessible to external devices since smartcard 50 does not contain either the key used to encrypt the data or information from which that key can be derived.

This level of security however does have the disadvantage that a system failure which prevents communication with the Trusted Authority would prevent any access to the encrypted information. Accordingly, in other embodiments of the subject invention the smartcard of individual P or of provider H may store the key used to encrypt certain sensitive, critical, information, and maybe programmed to decrypt and output this information for certain providers who are certified by the Certifying Authority as having emergency authorization to access such information even in the event of a system failure. For example, the head of an emergency medical service might have authority to access such sensitive, critical data in the event of a system failure while other medical personal could only access such data with an access code issued by a Trusted Authority, but without needing immediate access to the Trusted Authority. Of course, non-sensitive information, such as blood type, can simply be printed on the face of the card.

Figure 7A:
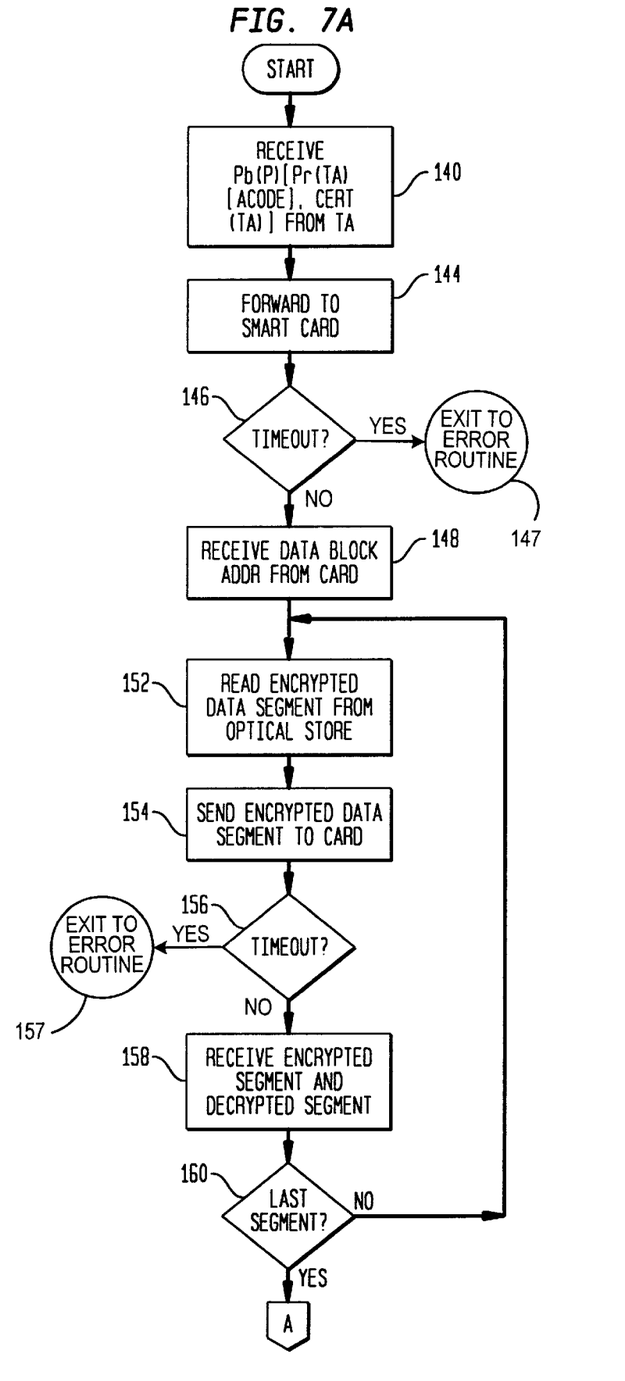
FIGS. 7a and 7b show a flow diagram of the operation of the terminal of a service provider when information is read from the smartcard of FIG. 3.
Figure 7B:
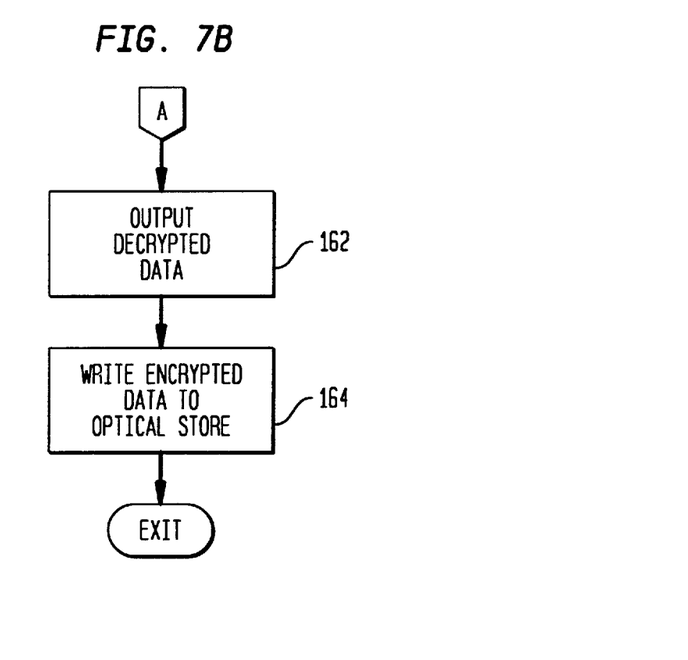

Turning to FIGS. 7a and 7b, a flow diagram of the operation of controller 16 as it interacts with smartcard 50 to read data is shown. At 140, controller 16 receives the encryption of ACODE and the certificate of the Trusted Authority from the Trusted Authority, and, at 144, forwards it to the smartcard.

If no response is received from the smartcard within a predetermined time period, at 146 controller 16 exits to error routine 147. Otherwise, at 148 the data block address and size are received from smartcard 50, and at 152 controller 16 reads an encrypted data segment comprised in the data block from optical store 158. Then, at 154 the encrypted data segment is sent to microprocessor 52.

Again, if no response is received, at 156 controller 16 exits to error routine 157.

Otherwise, at 158 the re-encrypted data segment (i.e. the data segment re-encrypted with NSK) and the decrypted data segment are returned from smartcard 50.

At 160 controller 16 determines if this is the last segment and if not returns to 152 to read the next data segment.

Once the last data segment is received, at 162 controller 16 assembles and outputs all the decrypted data segments, and at 164 writes the re-encrypted data to Optical Data Store 58, and then exits.

Figure 8:
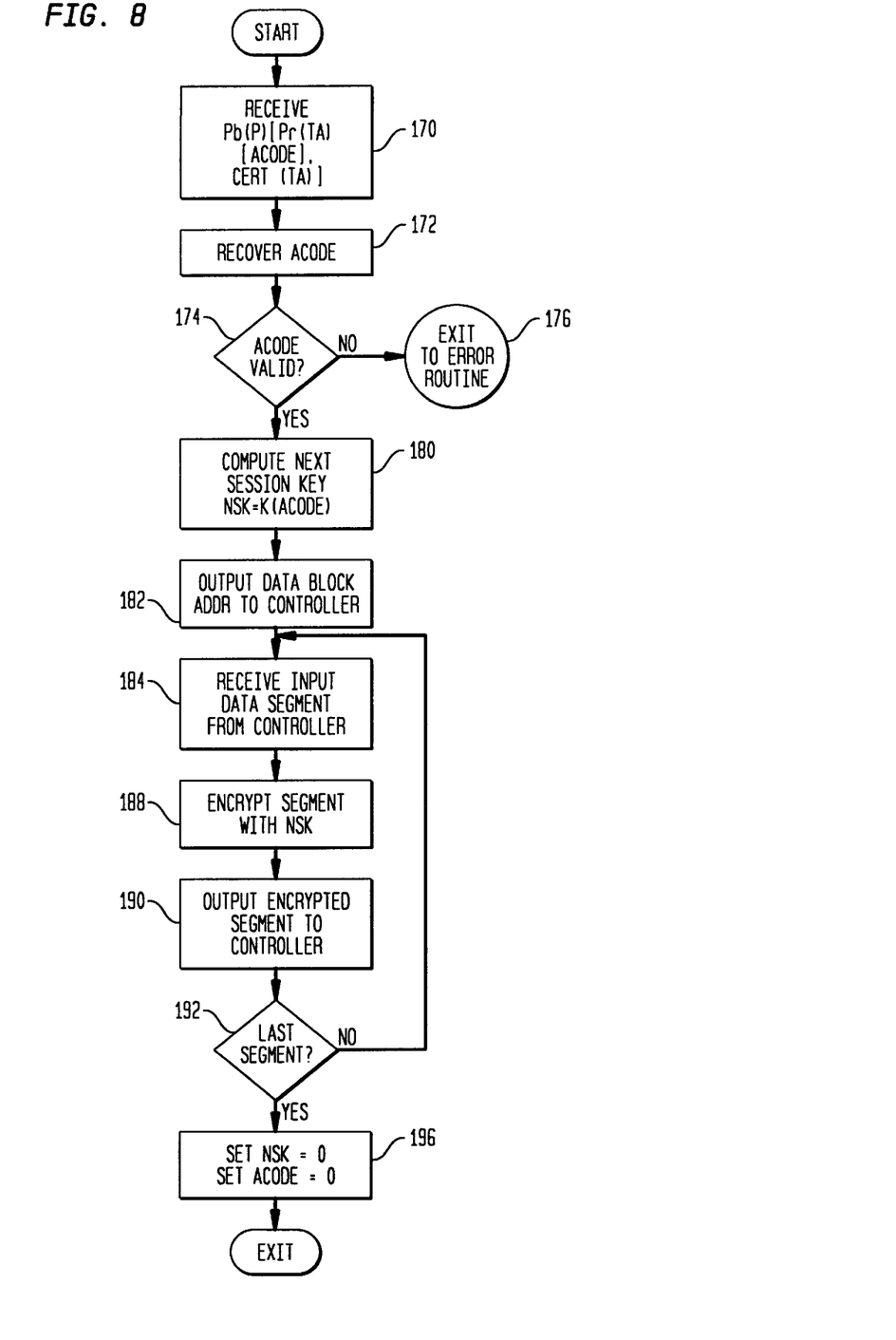
FIG. 8 shows a flow diagram of the operation of the smartcard of FIG. 3 when information is written to the smartcard.

Turning to FIG. 8 a flow diagram of the operation of smartcard 50 as it interacts with controller 16 to write data is shown.

Those skilled in the art will recognize that the operation of smartcard 50 in executing elements 170 through 182 is identical to the operation shown in FIG. 6a in executing elements 110 through 122 and that these elements can be implemented using common program modules. However, they have been shown as separate elements in separate flow diagrams here for purposes of ease of description.

After the data block address and size are output to controller 16 at 182, at 184, smartcard 50 receives an input data segment from controller 16. AT 188 the segment is encrypted with NSK. At 190 the encrypted segment is output to controller 16 and at 192, smartcard 50 determines if this is the last data segment. If not smartcard 50 returns to 184 to input the next data segment.

Once the last segment is received NSK and ACODE are set to 0 at 196, and smartcard 50 exits.

Figure 9:
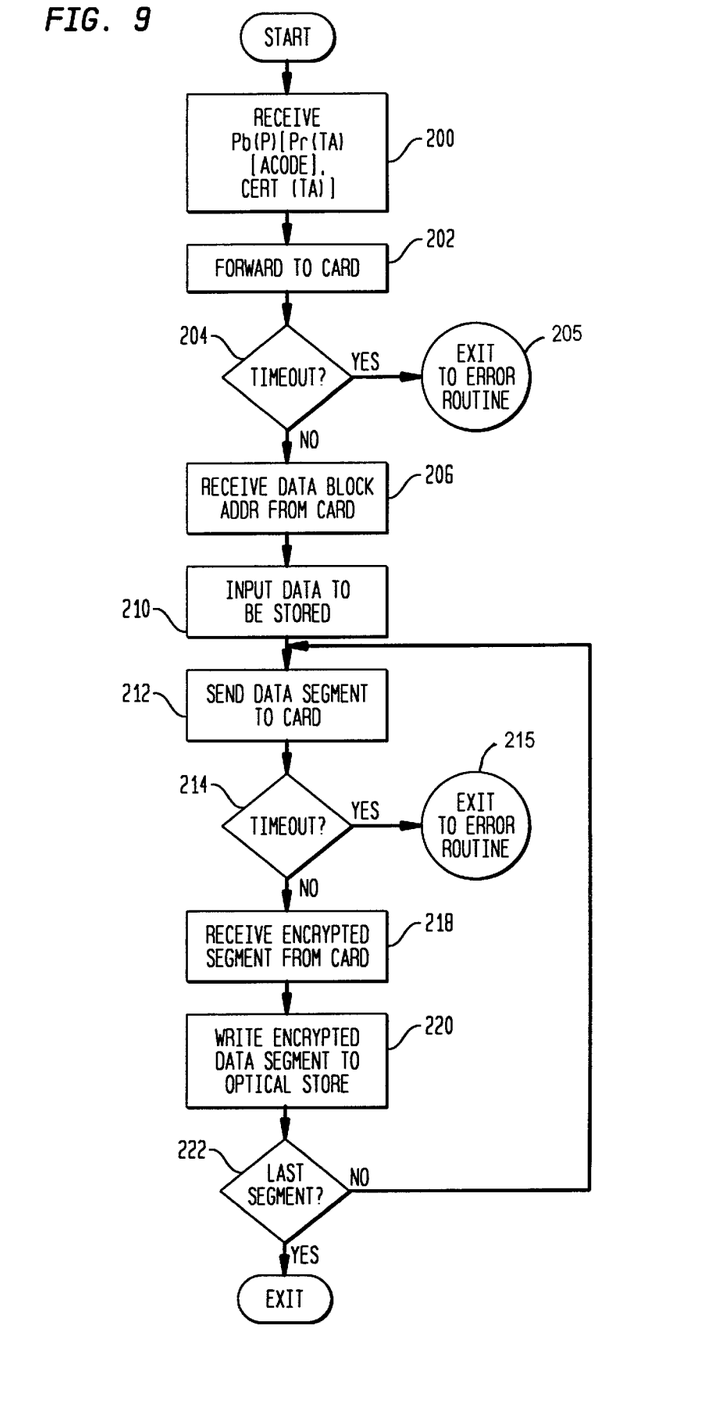
FIG. 9 shows a flow diagram of the operation of the terminal of a service provider when information is written to the smartcard of FIG. 3.

Turning to FIG. 9 a flow diagram of the operation of controller 16 as it cooperates with the smartcard to input data is shown. Again, those skilled in the art will recognize that the execution of elements 200 through 206 is identical to the execution of elements 140 through 146 in FIG. 7a; but is again shown separately here for ease of description.

After the data block address and size are received from smartcard 50 then, at 210, the data to be stored is input, and, at 212, is partitioned into data segments suitable to be operated on by the encryption algorithm used.

At 214, if the smartcard does not respond in a predetermined time controller 16 exits to error routine 215.

Otherwise, at 218, controller 16 receives the encrypted data segment from smartcard 50 and, at 220, writes the encrypted data segment to optical store 58.

At 222 controller 16 determines if this is last segment and, if not, returns to 212 to send the next data segment to smartcard 50, and otherwise exits.

Preferably, data stored in optical data store 58 is encrypted using a single key encryption algorithm such as DES.

It should be noted that in the embodiment described above encryption of messages transmitted between various parties has been used primarily to authenticate the messages. Thus, no further encryption of data such as various certificates has been used in the above described embodiments, and such elements must be presumed available to outside parties wishing to attack the system. In other embodiments of the subject invention encryption techniques can be used to overcome this problem. For example, as is known, all messages between parties may be encrypted with the public key of the receiving party who then decrypts the messages with a secret, private key.

This protects the message from third parties, but since public keys are by definition public, does not provide assurance that a message actually originates from the putative sender. This, as is also known, can be achieved by encrypting each message with the private key of the sender and appending a certificate provided by a Certifying Authority as has been described above. Successful decryption of the message provides assurance that the message did originate in fact with the punitive sender but the message is accessible to third parties who have the Certifying Authorities' public key. Of course, messages may be encrypted using both techniques to provide both security and authentication and these and other known encryption techniques may be applied to messages communicated between parties in various embodiments of the subject invention.

Those skilled in the art will recognize that security of the system of the subject invention is based upon security of the various private keys. Accordingly, keys should be distributed to the parties in a secure manner and kept secure by the parties. Many methods for distributing keys and maintaining security of keys are known, and any convenient methods for maintaining security of keys may be used in conjunction with the subject invention and particular key security methods used with the subject invention form no part of the subject invention per se.

Presently it is contemplated that initialization will be carried out by controlled transfer of media with Certifying Authorities initializing Trusted Authorities, Trusted Authorities initializing Service Providers, and Service Providers initializing individuals.

The above descriptions and drawings of preferred embodiments have been provided by way of illustration only and numerous other embodiments of the subject invention will be apparent to those skilled in the art from consideration of the above description and the attached drawings. Accordingly, limitations on the subject invention are to be found only in the claims set forth below.

What is claimed is:

1. A system for recording information and controlling access to said information, said system comprising:
   a) a portable recording medium including memory for storing encrypted individual user information locally and a microprocessor, said microprocessor being responsive to input of an access code to enable access to said encrypted information;
   b) a remote data processing center including a database of a plurality of authorized service providers with respect to said information; and a plurality of access codes corresponding to each of said plurality of authorized service providers, said access codes including a key for decrypting said encrypted information;
   c) said database being created under the direction of said individual user;
   d) a terminal communicating between said portable recording medium and said processing center; wherein
   e) said processing center being responsive to a request initiated at said terminal by said service provider for access to said encrypted information, said data processing center accessing said database to determine if said identified service provider is authorized to access said encrypted information, and to output said access code to said identified service provider only if said identified service provider is authorized to access said encrypted information;
   f) whereby accessing and decrypting said encrypted information at said portable medium only through use of said obtained access code.

2. A system as described in claim 1 wherein said processing center is controlled by a third party distinct from at least some of said service providers identified in said database.

3. A system as described in claim 2 wherein said third party possesses a certificate issued by a certifying authority, said certificate serving to establish the identity and trustworthiness of said third party.

4. A system as described in claim 1 wherein said portable recording medium is a smart card.

5. A system as described in claim 1 wherein said portable recording medium includes a writable optical memory.

6. A system as described in claim 1 wherein said information is medical information.

7. A system for recording information and controlling access to said information, said system comprising:
   a) a portable recording medium including memory for storing encrypted information and a microprocessor, said microprocessor being responsive to input of an access code to enable access to said encrypted information;
   b) a remote data processing center including a database of a plurality of authorized service providers with respect to said information; and a plurality of authorization codes corresponding to each of said plurality of service providers, said access codes including a key for decrypting said encrypted information;
   c) said database being created under the direction of said individual user;
   d) a terminal communication between said portable recording medium and said processing center; wherein
   e) said processing center being responsive to said request initiated at said terminal by said service provider for access to said encrypted information, said request identifying a service provider seeking emergency access to said information, to output said access code without regard to authorization of said service provider seeking emergency access, said access code enabling access to at least a predetermined part of said encrypted information; and
   f) said processing center recording at least a time and an identity for service provider seeking emergency access.

8. A method for controlling access to recorded information, said method comprising the steps of:
   a) establishing a remote data processing center;
   b) receiving at said data processing center data identifying service providers who can request access to encrypted information and second data identifying levels of authorization corresponding to said service providers who can access said encrypted information;
   c) said database being created under the direction of said individual user
   d) providing an individual user with a portable recording medium including memory for storing said encrypted information and a microprocessor, said microprocessor being responsive to input of an access code to enable access to said encrypted information;
   e) receiving a message from one of said service providers requesting access to said encrypted information, said encrypted information having been stored in said memory;
   f) accessing said database to determine if said one of said service provider is authorized to access said encrypted information;
   g) if said one of said service providers is authorized to access said encrypted information, providing said access code to said one of said service providers for accessing and decrypting said encrypted information contained in said portable medium.

9. A method as described in claim 8 comprising the further steps of:
   a) assigning a distinct public key pair including a public key and a privat key to each of said service providers for which said first data is accurate, whereby said request can be digitally signed with a private key assigned to said one of said service providers;
   b) verifying that said request is signed with said private key assigned to said one of said service providers; and
   c) accessing said data base to determine if said one of said service providers is authorized to access said information only if said request is successfully verified.

10. A method as described in claim 8 wherein a different key is required to decrypt said information for each access to said information.

11. A method as described in claim 8 wherein each service provider authorized to access said information is provided with a public key pair including a public key and a private key and said request is digitally signed by said identified service provider with a private key provided to said authorized service provider.

12. A method as described in claim 8 herein said portable recording medium is a smart card.

13. A method as described in claim 8 wherein said portable recording medium includes a writable optical memory.

14. A method as described in claim 8 wherein said information is medical information.

15. A system for recording information and controlling access to said information, said system comprising:
   a) a portable recording medium including memory for storing individual user information locally, said information being encrypted with a current session key, and a microprocessor, said microprocessor being responsive to input of an access code, said access code comprising said current session key, to enable access to said information;
   b) a remote data processing center including a database of a plurality of authorized service providers with respect to said information; and a plurality of authorization codes corresponding to each of said plurality of service providers;
   c) said database being created under the direction of said individual user
   d) a terminal communication between said portable recording medium and said processing center; wherein
   e) said processing center being responsive to a request initiated at said terminal by said service provider for access to said information, said data processing center accessing said database to determine if said identified service provider is authorized to access said information, and to output said access code to said identified service provider only if said identified service provider is authorized to access said information, said service provider inputting said access code to said microprocessor to access said information.

16. A system as described in claim 15 wherein said microprocessor decrypts said information with said current session key, outputs said decrypted information to said service provider, and re-encrypts said decrypted information with a next session key prior to rewriting said information to said memory, said next session key being determined as a predetermined function of access session information, said microprocessor then deleting said next session key, whereby said microprocessor cannot again decrypt said re-encrypted information until a new access code is input; and wherein further said data processing center also determines said next session key in accordance with said predetermined function and said access session information, whereby said data processing center is able to provide said new access code.

17. A system as described in claim 16 wherein at least a part of said access session information is comprised in said access code.

18. A system as described in claim 16 wherein said access session information comprised in said access code includes a unique access sequence number.

19. A method for controlling access to recorded information, said method comprising the steps of:
   a) establishing a remote data processing center;
   b) receiving at said data processing center, first data identifying service providers who can request access to said information and second data identifying levels of authorization corresponding to said service providers who can access said information;
   c) providing an individual user with a portable recording medium including memory for storing said information, said information being encrypted with a current session key, and a microprocessor, said microprocessor being responsive to input of an access code, said access code comprising said current session key to enable access to said information;
   d) said database being created under the direction of said individual user
   e) receiving a message from one of said service providers requesting access to said information, said information having been stored in said memory;
   f) accessing said database to determine if said one of said service providers is authorized to access said information;
   g) if said one of said service providers is authorized to access said information, providing said access code to said one of said service providers; said service provider inputting said access code to said microprocessor to access said information.

20. A method as described in claim 19 wherein said microprocessor decrypts said information with a current session key, outputs said decrypted information to said service provider, and re-encrypts said decrypted information with a next session key prior to rewriting said information to said memory, said next session key being determined as a predetermined function of access session information, said microprocessor then deleting said next session key, whereby said microprocessor cannot again decrypt said re-encrypted information until a new access code is input; and wherein further said data processing center also determines said next session key in accordance with said predetermined function and said access session information, whereby said data processing center is able to provide said new access code.

21. A method as described in claim 20 wherein at least a part of said access session information is comprised in said access code.

22. A method as described in claim 21 wherein said information access session comprised in said access code Includes a unique access sequence number.

* * * * *